US00PP14941P2

(12) United States Plant Patent
Olesen et al.

(10) Patent No.: US PP14,941 P2
(45) Date of Patent: Jun. 22, 2004

(54) MINIATURE ROSE PLANT NAMED 'POULRA014'

(50) Latin Name: *Rosa hybrida*
Varietal Denomination: POULra014

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/264,009

(22) Filed: Oct. 2, 2002

(51) Int. Cl.[7] ..... A01H 5/00
(52) U.S. Cl. ..... Plt./121
(58) Field of Search ..... Plt./121, 116, 128

*Primary Examiner*—Bruce R. Campell
*Assistant Examiner*—June Hwu

(57) ABSTRACT

A new miniature rose plant which has abundant, lavender flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Classification: Botanical: *Rosa hybrida* 'POULra014'. Commercial: Miniature.

SUMMARY OF THE INVENTION

The present invention constitutes a new and distinct variety of miniature rose plant which originated from a controlled crossing between 'KORstoffein', described and illustrated in U.S. Plant Pat. No. 11,242 issued on Feb. 22, 2000 and an unnamed seedling (not patented). The two parents were crossed and the resulting seeds were planted in a controlled environment. The new variety is named 'POULra014'.

The new rose may be distinguished from its seed parent, 'KORstoffein', by the following combination of characteristics:

1. The bloom color of 'KORstoffein' is yellow-orange, while that of 'POULra014' is lavender.
2. The petal count for 'KORstoffein' is 25 to 30, while that of 'POULra014' is 30 to 35.
3. The bud color of 'KORstoffein' is Red Group 52D, while that of 'POULra014' is Red-Purple Group 62D.

The new rose may be distinguished from its pollen parent, by the following combination of characteristics:

1. 'POULra014' is shorter in height than the pollen parent.
2. 'POULra014' has a general tonality of Red-Purple Group 62D, while the pollen parent has a general tonality of Red-Purple Group 69D.

The objective of the hybridization of this rose variety for commercial culture was to create a new and distinct variety with unique qualities, such as:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type and distinguish 'POULra014' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULra014' was selected by the inventors as a single plant from the progeny of the hybridization in 1998.

Asexual reproduction of 'POULra014' by cuttings and traditional budding was first done by L. Pernille and Mogens N. Olesen in their nursery in Fredensborg, Denmark in Spring of 1999. This initial and other subsequent propagations conducted in controlled environments have demonstrated that the characteristics of 'POULra014' are true to type and are transmitted from one generation to the next.

BRIEF DESCRIPTION OF THE DRAWING

The accompanying color illustration shoes as true as is reasonably possible to obtain in color photographs of this type, the typical characteristics of the buds, flowers, leaves, and stems of 'POULra014'. Specifically illustrated in SHEET 1:

1. Stem showing branching and the attachment of leaves, buds, and peduncles;

2. Flower bud, partially opened bud, and open bloom;

3. Flower petals, detached;

4. Sepals, receptacle, and pedicel;

5. Stem as well as a bare stem exhibiting thorns;

6. Leaves.

DETAILED DESCRIPTION OF THE VARIETY

The following is a description of 'POULra014', as observed in its growth in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety 'POULra001', a rose variety from the same inventors described and illustrated in U.S. Plant Pat. No. 13,487 dated Jan. 21, 2003 are compared to 'POULra014' in Chart 1.

CHART 1

| | 'POULra014' | 'POULra001' |
|---|---|---|
| General Tonality: | Red-Purple Group 62D. | Red Group 50D |
| Petal Count | 30 to 35 petals. | 50 to 60 petals. |
| Bud Color | Red-Purple Group 62D. | Red Group 39B. |

Parents: 'KORstoffein'×an unnamed seedling.

FLOWER AND FLOWER BUD

Blooming habit: Continuous.

Flower bud:

*Size.*—Upon opening, 25 to 30 mm in length from base of receptacle to end of bud.

*Bud form.*—Ovoid.

*Bud color.*—As sepals unfold, Red-Purple Group 62D; At ¼ opening, Red-Purple Group 62D.

*Sepals.*—Upper surface: Green Group 137B at margins, Yellow-Green Group 144D in center. Lower surface: Yellow-Green Group 144A. Weak foliaceous appendages on three of the five sepals. Surfaces of sepals slightly pubescent. Stipitate glands are present at edges of sepals and foliaceous extensions. Shape: Sepal apex is cirrose. Base is flat at union with peduncle. Size: 27 mm long×10 mm wide.

*Receptacle.*—Surface: Smooth. Shape: Funnel shaped. Size: 6 mm (h)×8 mm (w). Color: Yellow-Green Group 146C.

*Peduncle.*—Surface: Fine white hairs and stipitate glands present. Length: 30 to 35 mm average length. Color: Yellow-Green Group 146B. On plants grown under high light conditions, peduncle may exhibit intonations of Red-Purple Group 59B. Strength: Strong.

*Borne.*—Singly.

*Anthocyanin.*—Greyed Red Group 178B.

Flower bloom:

*Fragrance.*—None from bloom; stipitate glands produce faintly resinous fragrance.

*Duration.*—As a pot plant, flowers last from 18 to 22 days. Petals fall cleanly away from plant.

*Size.*—Medium for a 10.5 cm pot rose. Average flower diameter is 65 mm when open.

*Form.*—Shape of flower when viewed from the side: Upon opening, upper part: Flattened. Upon opening, lower part: Convex. Open flower, upper part: Flattened. Open flower, lower part: Concave.

*Petalage.*—Average range: 30 to 35 petals under normal conditions with 5 to 7 petaloids.

Color:

*Upon opening, petals.*—Outermost petals: Outer Side: Red-Purple Group 62D, with an occasional rib of Yellow Group 2D. Inner Side: Red-Purple Group 65D. Innermost petals: Outer Side: Red-Purple Group 62D. Inner Side: Red-Purple Group 65D.

*Upon opening, basal petal spots.*—Outermost petals: Outer Side: Yellow Group 4B. Inner Side: Yellow Group 4B. Innermost petals: Outer Side: Yellow Group 4B. Inner Side: Yellow Group 4B.

*After opening, petals.*—Outermost petals: Outer Side: Red-Purple Group 65B. Inner Side: Red-Purple Group 65D. Innermost petals: Outer Side: Red-Purple Group 65B. Inner Side: Red-Purple Group 62D.

*After opening, basal petal spots.*—Outermost petals: Outer Side: Yellow Group 1D. Inner Side: Yellow Group 1D. Innermost petals: Outer Side: Yellow Group 1D. Inner Side: Yellow Group 1D.

General Tonality: On open flower Red-Purple Group 62D. No change in the general tonality at the end of the $7^{th}$ day. Afterwards, general tonality is Red-Purple Group 65D.

Petals:

*Petal reflex.*—Strong.

*Petal edge.*—Entire.

*Petal size.*—26 mm in length by 22 mm wide.

*Shape.*—Rounded obovate. Apex is Rounded. Base is Rounded.

*Surface texture.*—Smooth.

*Petaloids.*—Quantity: 5 to 7. Size: 8 mm long×5 mm wide. Color: Red-Purple Group 62C.

*Thickness.*—Moderately thick.

*Arrangement.*—Formal.

Reproductive Organs:

*Pistils.*—Length: 5–6 mm long. Quantity: 25 to 30.

*Pollen.*—Color: Greyed-Orange Group 163A. Quantity: Average.

*Anthers.*—Size: 2 mm long. Color: Greyed-Yellow Group 160B. Quantity: 20 to 25.

*Filaments.*—Color: Yellow Group 2B. Length: 5 to 7 mm.

*Stigmas.*—Approximately even in height with anthers. Color: Orange-White Group 159D.

*Styles.*—Color: Green Group 142C.

*Seed formation.*—Hips: None observed.

PLANT

Plant growth: Vigorous, compact, upright to bushy. When grown as a 10.5 cm pot plant, the average height of the plant is 25 to 30 cm and the average width is 25 cm.

Stems:

*Color.*—Young wood: Yellow-Green Group 145A, with occasional Greyed-Red Group 182 A and B. Older wood: Yellow-Green Group 146B and C.

*Thorns.*—Incidence: 1 to 2 thorns per 10 cm of stem. Size: Average length: 4 mm. Color: Greyed-Yellow Group 160D, with intonations of Greyed-Red Group 182B. Shape: Linear.

*Surface.*—Young wood: Smooth. Older wood: Smooth.

Plant foliage: Normal number of leaflets on leaves in middle of the stem: 5 leaflets.

*Leaf size.*—70 mm (l)×45 mm (w).

*Quantity.*—Average.

*Color.*—Upper Leaf Surface: Green Group 137B. Lower Leaf Surface: Green Group 138B. Juvenile foliage: Upper Leaf Surface: Yellow-Green Group 146C. Lower Leaf Surface: Yellow-Green Group 146D. Anthocyanin intonation: Location: On plants grown under high light conditions, leaf margins, peduncles, and stems may exhibit intonations of Greyed-Purple Group 183B.

Plant leaves and leaflets:

*Stipules.*—Size: 15 mm long. Color: Points are Yellow-Green Group 146A; base is Yellow-Green Group 146D, and interior is Greyed-Green Group 195C. Stipitate glands: Present on edges of stipules.

*Petiole.*—Length: 11 to 12 mm. Color: Margins are Yellow-Green Group 146A; base is Yellow-Green Group 146D, and interior is Greyed-Green Group 195C. Underneath: Yellow-Green Group 146D. Margins: Stipitate glands present.

*Rachis.*—Color: Margins are Yellow-Green Group 146A; base is Yellow-Green Group 146D, and interior is Greyed-Green Group 195C. Underneath: Yellow-Green Group 146D. Margins: Stipitate glands present.

*Leaflet.*—Edge: Serrated. Shape: Ovate. Apex is round to attenuate. Base shape is mucronate to acute. Texture: Smooth. Glossiness: Moderately glossy. Arrangement: Odd pinnate. Venation: Reticulate.

Disease resistance: Average resistance to mildew, black spot, and Botrytis under normal growing conditions in Jackson County, Oreg.

Cold tolerance: Know cold tolerance of the claimed plant is USDA plant hardiness zone 7.

What is claimed is:

1. A new and distinct variety of rose plant of the miniature class, substantially as herein illustrated and described as a distinct and novel rose variety due to its abundant, lavender flowers, vigorous growth, compact habit, suitability for production from softwood cuttings in pots, and durable flowers and foliage which make the variety suitable for distribution in the floral industry.

* * * * *

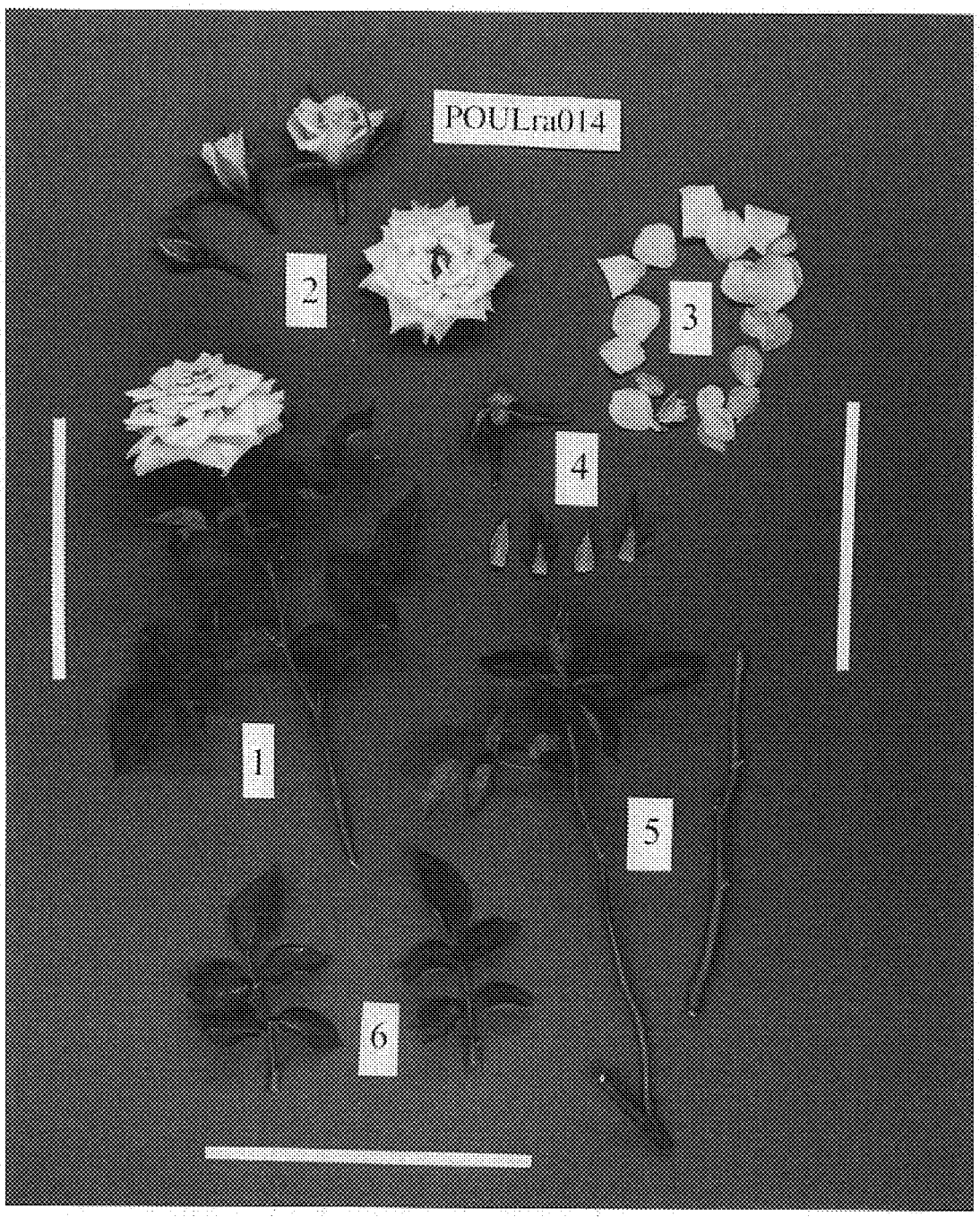
POULra014
1
2
3
4
5
6